United States Patent [19]
Harries

[11] Patent Number: 5,975,427
[45] Date of Patent: Nov. 2, 1999

[54] DEVICE FOR DISPENSING VOLATILE MATERIAL

[75] Inventor: Alun Harries, Camberley, United Kingdom

[73] Assignee: S. C. Johnson & Son, Inc., Racine, Wis.

[21] Appl. No.: 08/927,871

[22] Filed: Sep. 11, 1997

[51] Int. Cl.⁶ .................................................. A61L 9/12
[52] U.S. Cl. ........................................ 239/34; 206/274
[58] Field of Search .............................. 206/820, 0.5, 0.7, 206/216.1, 271, 274; 428/36.6, 36.7, 905; 239/34, 57, 68

[56] References Cited

U.S. PATENT DOCUMENTS

| | | |
|---|---|---|
| 2,431,924 | 12/1947 | Dunaway . |
| 2,626,833 | 1/1953 | Valentine ............................. 239/36 X |
| 2,809,863 | 10/1957 | Curran . |
| 2,878,061 | 3/1959 | Saeks . |
| 2,896,853 | 7/1959 | Curran . |
| 3,424,380 | 1/1969 | Curran . |
| 3,784,102 | 1/1974 | Stults .................................. 239/36 |
| 3,899,080 | 8/1975 | Brunda .................................. 206/531 |
| 3,921,805 | 11/1975 | Compere .............................. 206/532 |
| 4,157,787 | 6/1979 | Schwartz ............................. 239/60 X |
| 4,158,440 | 6/1979 | Sullivan et al. . |
| 4,161,283 | 7/1979 | Hyman . |
| 4,285,468 | 8/1981 | Hyman . |
| 4,583,686 | 4/1986 | Martens et al. . |
| 4,634,614 | 1/1987 | Holzner ............................... 239/57 X |
| 4,653,644 | 3/1987 | Sullivan et al. ....................... 239/60 X |
| 4,722,477 | 2/1988 | Floyd .................................. 239/36 |
| 4,804,142 | 2/1989 | Riley .................................. 239/56 |
| 4,821,884 | 4/1989 | Griffin et al. . |
| 5,115,976 | 5/1992 | Weiss et al. . |
| 5,316,148 | 5/1994 | Neumann et al. . |
| 5,518,790 | 5/1996 | Huber et al. ....................... 239/57 X |
| 5,711,955 | 1/1998 | Karg . |

FOREIGN PATENT DOCUMENTS

| | | |
|---|---|---|
| 82111287 | 6/1982 | European Pat. Off. . |
| 92300314 | 1/1992 | European Pat. Off. . |
| 94420260 | 9/1994 | European Pat. Off. . |
| 1574108 | 4/1968 | France . |
| 1568938 | 12/1968 | France . |
| 74 07031 | 3/1974 | France . |
| 85 12311 | 4/1985 | France . |
| 85 16013 | 10/1985 | France . |
| 1042851 | 2/1957 | Germany ............................. 239/56 |
| 44 06 581 A1 | 7/1995 | Germany . |
| 1053550 | 9/1988 | United Kingdom . |
| 2 161 383 | 7/1995 | United Kingdom . |
| WO 84/02654 | 1/1984 | WIPO . |

*Primary Examiner*—Kevin Weldon

[57] ABSTRACT

A device for dispensing volatile material from a reservoir which has a dispensing portion from which the vapor of the volatile material can diffuse into the surrounding atmosphere. The reservoir is retained on a rigid sheet which has a suspending aperture with a slot. There is a removable impermeable layer for sealing the dispensing portion and a detachable portion of the rigid sheet extends over the dispensing portion of the reservoir. In another embodiment, there are two such devices detachably attached by a joint to each other at an edge.

13 Claims, 5 Drawing Sheets

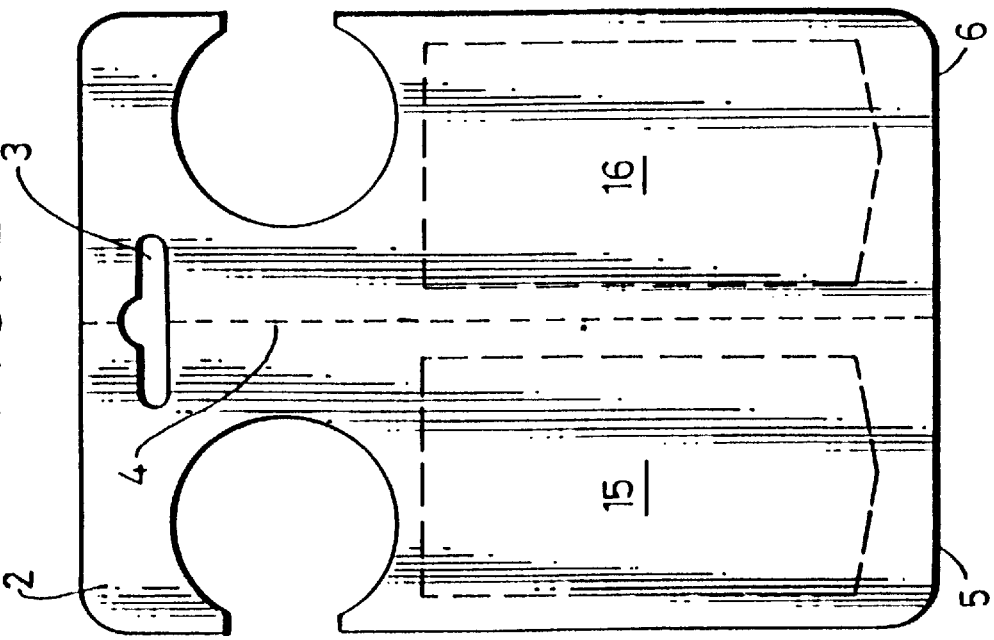
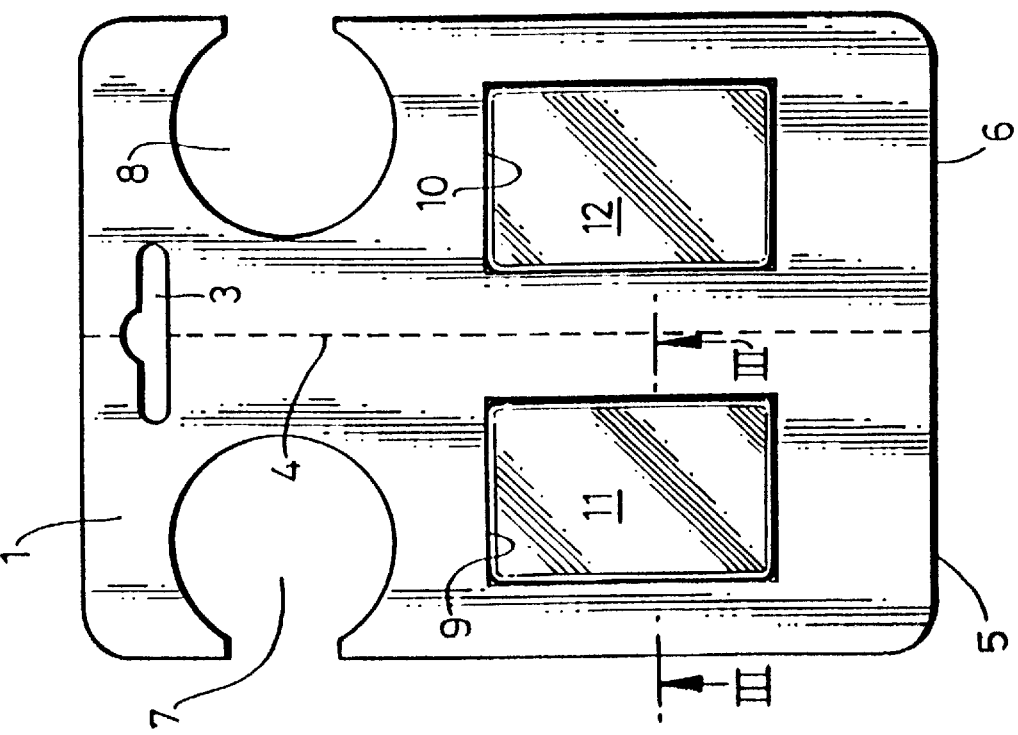

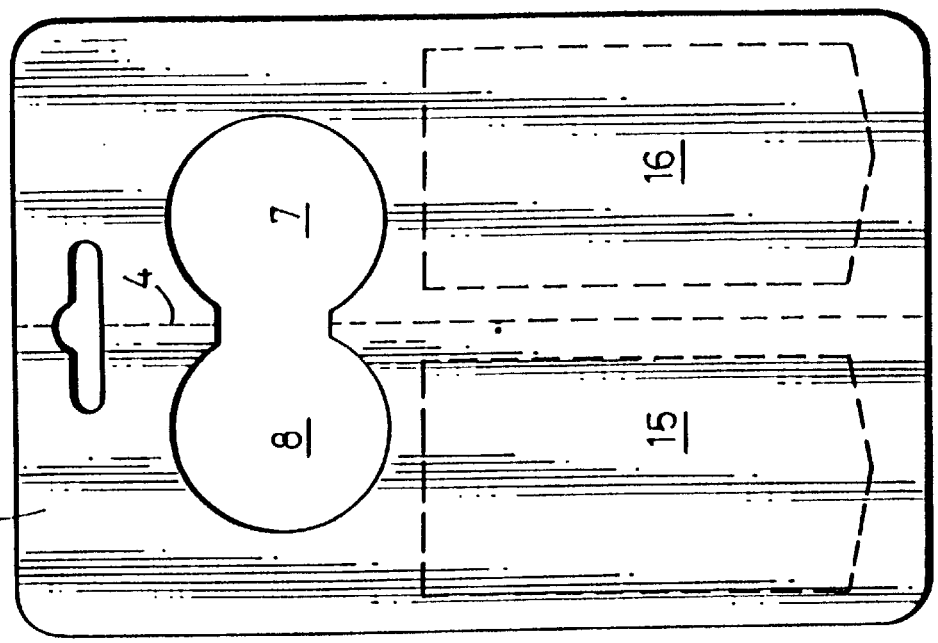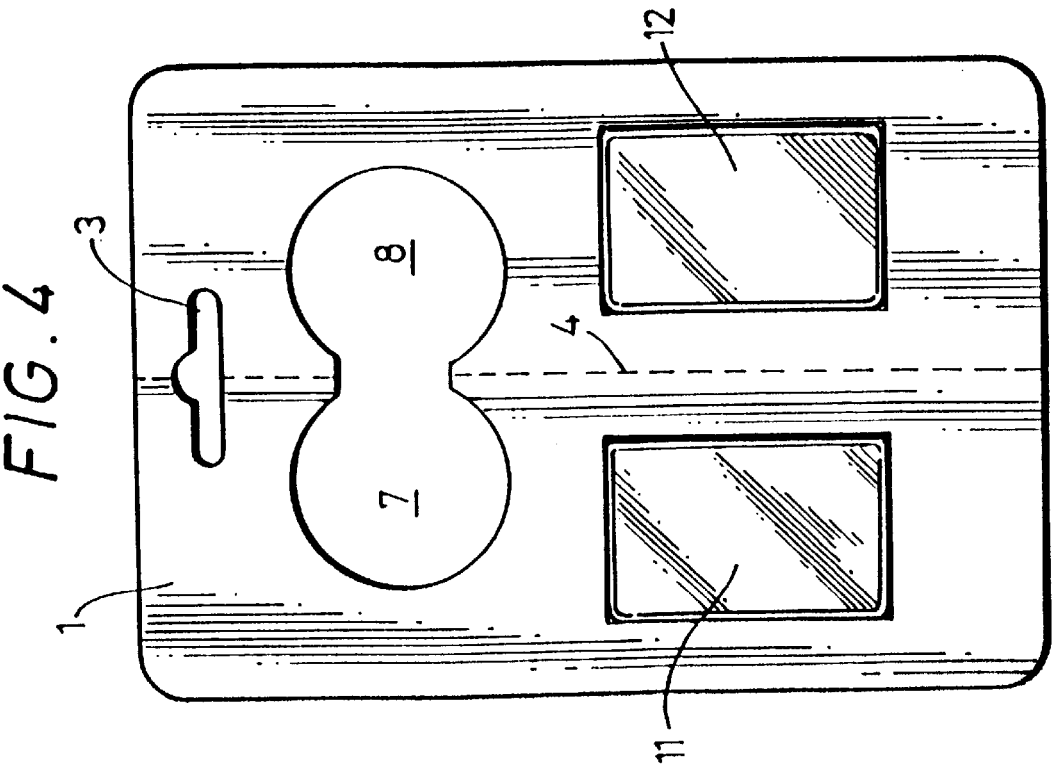

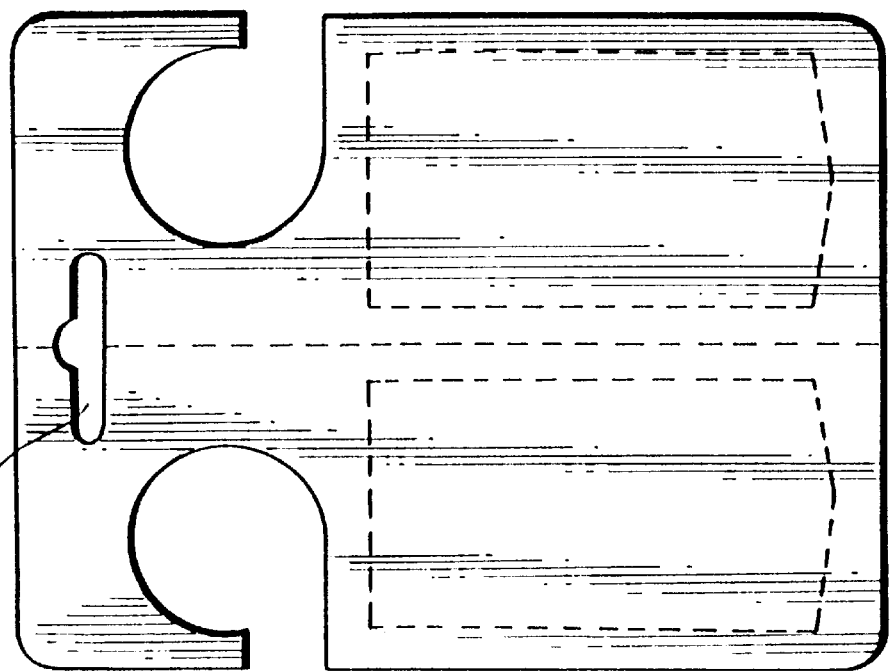
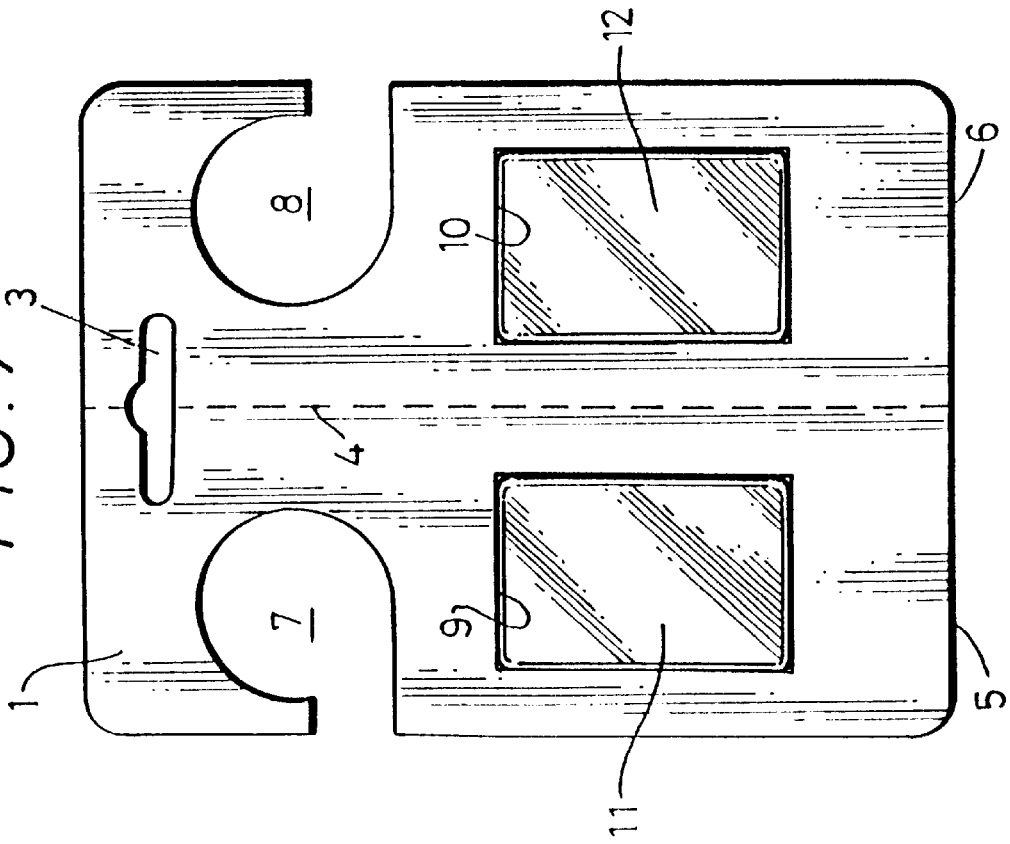

DEVICE FOR DISPENSING VOLATILE MATERIAL

This present invention relates to a device for dispensing volatile material.

BACKGROUND ART

It is desirable to provide an improved device for dispensing volatile materials, e.g., insecticides, which uses simple packaging and which minimizes the risk of contact with volatile material.

DISCLOSURE OF INVENTION

According to the present invention, a device for dispensing volatile material comprises:

a) a reservoir containing volatile material, said reservoir having a dispensing portion from which vapour of the volatile material can diffuse into the surrounding atmosphere;

b) a removable impermeable layer for sealing said dispensing portion;

c) a substantially flat and rigid sheet; said sheet having
  i) means for retaining the reservoir on the sheet in use;
  ii) an opening by which it may be suspended in use;
  iii) preferably, a detachable portion extending over the dispensing portion and the impermeable layer such that removal of the detachable portion from the sheet enables the impermeable layer to be removed from the dispensing portion.

The reservoir may be a moulding of thermoplastic polymer of the type used in conventional blister packs. The volatile material will generally be present in the reservoir in a carrier in which it is dissolved or dispersed. The carrier may be a liquid in which the volatile material is dispersed or dissolved, and may be a relatively viscous liquid. Alternatively, the carrier may, for example, be a solid gel, or a card impregnated with the volatile material. The preferred carrier will depend on the nature of the volatile material. The volatile material may be an insecticide, e.g., a permethrin insecticide, or a perfume, or may be a combination of an insecticide and a perfume. The device of the present invention may be particularly useful where the volatile material in the reservoir is a material, such as an insecticide, which it is desirable to avoid coming into contact with the skin.

Where a liquid is used in the reservoir then the dispensing portion of the reservoir may be a sheet of material which allows volatile material to pass through but retains the liquid.

As indicated above, the carrier in the reservoir may be a solid in which the volatile material is dispersed and from which it diffuses with time and in such a case the dispensing portion may simply be an exposed face of the solid.

Layers which are impermeable to volatile materials and which are suitable for sealing the reservoir are well-known to those skilled in the art. Such layers usually contain metal, e.g., aluminum, which may be combined with a polymer layer.

Reservoirs or chambers containing volatile material, namely, perfume, together with a dispensing portion which is a polymer wall attached to the reservoir, and a removable impermeable layer are described in international patent application WO 84/02654. WO 84/02654 discloses a reservoir made of conventional polymers such as polyamide, polyester, polyethylene, or polypropylene. A permeable layer may be made from a polymer sold by the firm of E I du Pont de Nemours under the trade name "Surlyn". An impermeable layer may be aluminum sheet. A layer of paper is disclosed as being provided between the permeable layer and the impermeable layer.

As an alternative, the reservoir may be formed from an acrylonitrile copolymer sold under the trade name "Barex". A thin layer of polyethylene may be glued to the acrylonitrile copolymer to enable further layers to be heat sealed to the reservoir to close it. The reservoir may be closed by a laminate of ethylene/ethyl acrylate copolymer membrane, paper, low density polyethylene or "Surlyn" polymer, aluminum foil, and polyester. The low density polyethylene enables the aluminum foil to adhere to the paper. The aluminum foil, strengthened by the polyester, provided an impermeable layer. When using ethylene/ethylacrylate copolymer it is desirable to use non-polar volatile materials as the volatile material.

The substantially flat and rigid sheet may be formed from one or more layers of synthetic polymer, e.g., thermoplastic polymer. However, it is preferred that the sheet is formed from one or more layers of card, i.e., layers formed from wood pulp or similar cellulosic fibre.

The sheet preferably consists of two layers of card. A front layer is preferably provided with at least one window through which an exposed part of the reservoir extends. The reservoir is preferably provided with a flange extending round the exposed part in order to retain it within the window. A rear layer holds the reservoir in place between the front and rear layers. Alternatively, and with some advantage in materials and manufacturing costs and in simplicity of design, the sheet may consist of a single layer of card with the reservoir attached to it by any conventional means of attachment. If the single layer sheet construction is used, the optional detachable portion of the sheet referred to above is unnecessary. Instead, its protective function may be supplied by the use of a sealing layer that is sufficiently robust to withstand normal handling of the device before activation or by providing a second seal or some other protective layer, removably adhered to the back of the sheet and sufficiently large to cover the sealing layer and preferably the entire dispensing potion of the reservoir.

Preferably, the detachable portion of the sheet is a perforated portion in the sheet, e.g., in the rear layer of card where two layers of card are used, which defines a panel lying over the dispensing portion of the reservoir. Preferably, the panel is larger than the dispensing portion of the reservoir so that manual removal of the panel of the sheet to remove the sealing layer does not result in fingers coming into contact with the dispensing portion of the reservoir.

The panel may completely cover the impermeable layer and the removable impermeable layer may be provided with a tab by which it may be removed. The tab may be pulled to remove the impermeable layer after the panel has first been completely removed. The panel and the tab may be so disposed that partial removal of the panel exposes a sufficiently large tab to allow the remainder of the overlying panel to be removed by pulling on the tab to remove the impermeable layer lying under the panel. Alternatively, the panel may have an opening through which a tab on the impermeable layer projects so that pulling the tab causes the impermeable layer to detach from the dispensing portion and the movement of the impermeable layer away from the dispensing portion causes the overlying panel to become detached from the rest of the sheet. A further alternative is to bond the impermeable layer to the panel so that removal of the panel removes the impermeable layer.

In general, it is preferred that removal of one of a) the detachable portion of the sheet, and b) the impermeable layer, causes removal of the other of a) and b).

The sheet may be provided with a slot with a semi-circular central portion such as is conventional on packages intended to be displayed suspended on display units at the point of sale.

The sheet will normally carry printed matter identifying the product and giving instructions for its use and disposal. It is a feature of the present invention that the point of sale packaging can be used as the active device. As a result, instructions on the package are retained throughout the life of the device.

The suspending means is provided in the sheet itself, avoiding the need to fabricate a separate suspending device and to attach it to the reservoir. The suspending device is preferably provided by an aperture in the main body of the sheet rather than by portions of the sheet extending outwardly from the main body. Thus, when the sheet is of generally rectangular shape, the suspending device is preferably formed by an aperture within the rectangular main body rather than by portions projecting beyond the boundaries of the generally rectangular body. This is particularly advantageous when the sheet is formed from card.

The suspending means may be shaped to be hung on a hook or door handle but is preferably an aperture in the sheet shaped for suspending the device on a rail in a wardrobe. Such rails are generally circular.

The suspending means may be provided by a slot opening in the side of the sheet communicating with a larger aperture in the body of the sheet. The slot may be a simple slit having essentially no width, but, preferably, the slot is of such a width that it can receive a normal wardrobe rail without excessive flexing and may, for example, have a width of 5 to 15 mm. The larger aperture with which the slot communicates may, for example, have a substantially circular cross-section with a diameter in the range 20 mm to 40 mm.

It is preferred to provide packages comprising more than one device, e.g., two devices formed in a single sheet, which can be divided into individual device portions along at least one preformed line of division, e.g., by tearing along perforations provided in the sheet. In such multiple packages, the suspending means may be provided in the outer sides of the package. However, they may also be provided in the interior of the multiple package adjacent to any line of division demarking the contiguous sides of adjacent devices such that a suspending means opening from the side of a device is only formed when the package is divided into multiple devices.

BRIEF DESCRIPTION OF THE DRAWINGS

The invention will now be described with reference to the accompanying drawings in which FIG. 1 is a front elevation (assuming it to be hung vertically) of a package comprising two devices according to the invention, FIG. 2 is a rear elevation of the package.

DETAILED DESCRIPTION OF THE PREFERRED EMBODIMENT

Figure 3:
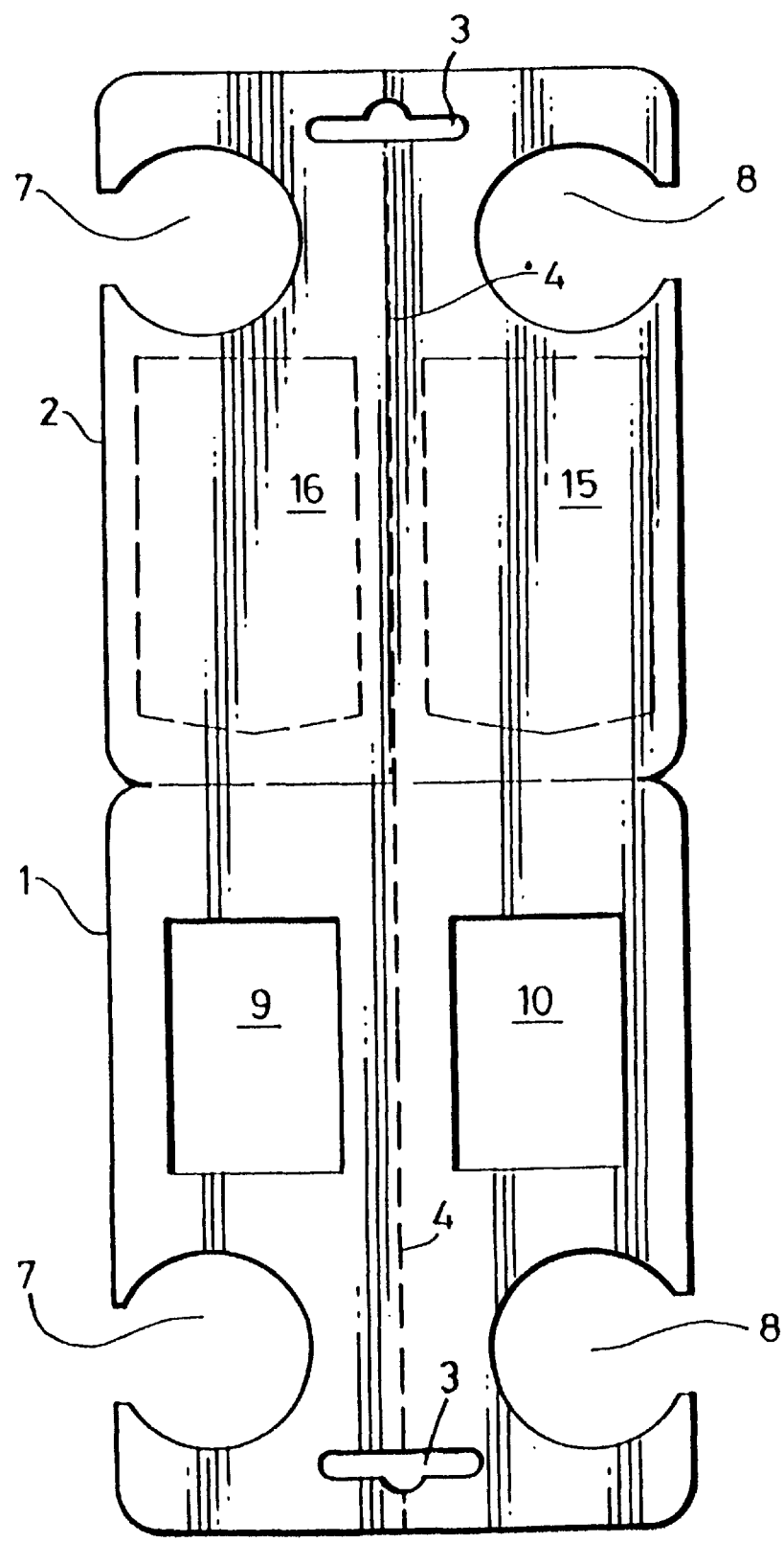
FIG. 3 shows a card blank suitable for making a multiple package corresponding to FIGS. 1 and 2, FIGS. 4 and 5 are front and rear elevations of card blanks corresponding to FIGS. 1 and 2, except that a single aperture in each blank is split when the package is divided into two devices to give a suspending means in each blank.

The package comprises a sheet formed from two layers of card (1,2) (formed from wood pulp) forming the front and rear faces of the package. The sheet (1,2) has a slot (3) formed in it by which it may be suspended from a suitable display unit at the point of sale. A line of perforations (4) runs vertically down both layers of card (1,2) to enable the package to be torn into two separate halves (5,6).

The sheet (1,2) has openings (7,8) formed in opposed upper sides. These provide suspending means by which the package as a whole or the separate portions (5,6) can be suspended on a rail in a wardrobe (clothes storage cupboard).

Figure 6:
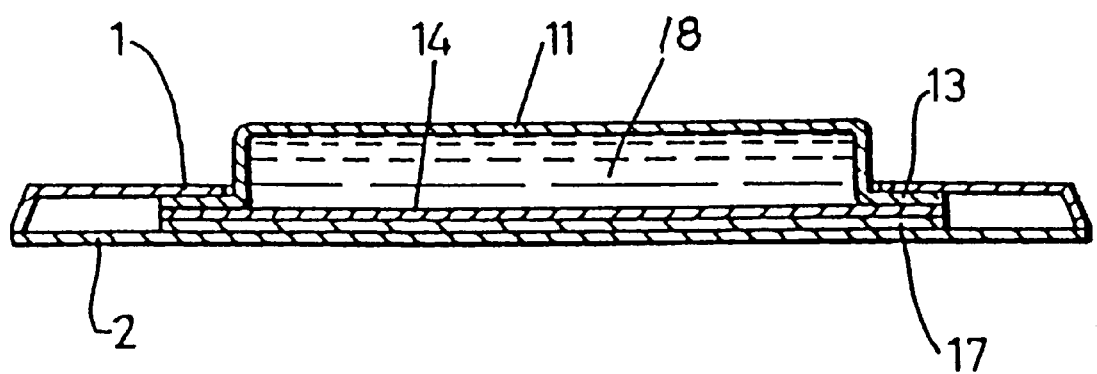
FIG. 6 is a cross-section (not to scale) along the line III—III in FIG. 1, FIG. 7 and 8 are front and side views of a package corresponding to FIGS. 1 and 2 but with a different design of suspending means.

The front layer (1) has two windows (9,10) provided by apertures in the layer. Two reservoirs (11,12) of moulded plastic material extend through the windows and are retained under layer (1) by flanges (13) (see FIG. 6) extending outwardly from the reservoir under layer (1).

Each reservoir (11,12) is closed at its rear face by a layer (14) of vapour permeable material which prevent the passage of liquid from the reservoirs but allow the passage of the volatile material to be released from the device. This layer (14) constitutes the dispensing portions of the reservoir. The reservoirs are filled with a liquid (18) in which is dissolved an active ingredient. When the device is intended for insect control, the active ingredient may be a volatile insecticide such as a permethrin insecticide.

The rear layer (2) is provided with perforations defining two removable panels (15,16). The panels lie over the corresponding rear faces area of reservoirs and the area of each rear panel is greater than that of the corresponding front window and of the corresponding dispensing portion.

Each layer (14) of permeable material on the rear of each reservoir is covered by a layer (17) of impermeable material, e.g., aluminized polymer film, which has a tab which may be gripped to remove the impermeable layer when the portion of the panel covering it has been removed.

In use, the package can be divided into two portions by tearing along line (4) and each half may be activated as required by removing the panel (15) or (16) to expose the impermeable layer to enable the layer to be removed. By making the panel large in relation to the size of the dispensing portion, the risk of fingers coming into contact with the permeable layer is reduced.

Instead of dividing the package before use, it may be used undivided by installing on a wardrobe rail using either of openings (7,8) and releasing volatile material from both reservoirs after removing the corresponding portions of layer (2) where a higher dose rate of insecticide is required in a larger wardrobe or releasing volatile material from each reservoir in succession to maintain a desired level of insecticide over a prolonged period of time.

It can be seen that the amount of packaging to be discarded when the device is first activated is small, and that fingers are kept away from the reservoir of volatile material when suspending the device in a wardrobe, when removing the impermeable layer to activate the device and on removing the exhausted device. The substantially rigid sheet provides a convenient means of manipulating the device as a whole. The specific embodiments described above have apertures for suspension opening from the sides of the sheet which are sized so as to enable the sheet to be hung on a conventional wardrobe rail (where there may be no access to a free end of the rail) without excessive flexing of the sheet. This enables the use of a material for the sheet such as card which is easily damaged by flexing. Because the apertures open from the side, the weight of the device is not supported by any portion of the card which might have suffered some flexing during mounting the device on a rail.

While preferred forms of the invention have been shown in the drawings and have been described above, variations will be apparent to those skilled in the art. Consequently, the invention should not be construed as limited to the specific forms shown and described. Instead, the invention should be understood in terms of the following claims.

I claim:

1. A device for dispensing volatile material which comprises:
   (a) a reservoir containing volatile material, said reservoir having a dispensing portion from which vapor of the volatile material can diffuse into the surrounding atmosphere;
   (b) a removable impermeable layer for sealing said dispensing portion; and
   (c) a substantially flat and rigid sheet, said sheet having:
      (i) means for retaining the reservoir on the sheet when in use;
      (ii) suspending means by which the device may be suspended in use, the suspending means including an aperture within the main body of the sheet and a slot opening from a side of the device communicating with the aperture in the sheet to allow the aperture to be accessible through the slot; and
      (iii) a detachable portion of the sheet extending over the dispensing portion of the reservoir and the removable impermeable layer, the detachable portion being detachable from the removable impermeable layer.

2. A device according to claim 1 wherein the volatile material comprises an insecticide.

3. A device according to claim 1 wherein the substantially flat and rigid sheet is formed from at least one layer of card.

4. A device according to claim 1 wherein the substantially flat and rigid sheet comprises
   a. a front layer of card with a window through which an exposed part of the reservoir extends, and
   b. a rear layer of card, the reservoir being held in place between the front and rear layers.

5. A device for dispensing volatile material which comprises:
   (a) a reservoir containing volatile material, said reservoir having a dispensing portion from which vapor of the volatile material can diffuse into the surrounding atmosphere;
   (b) a removable impermeable layer for sealing said dispensing portion;
   (c) a substantially flat and rigid sheet, said sheet having;
      (i) means for retaining the reservoir on the sheet when in use;
      (ii) suspending means by which the device may be suspended in use, the suspending means including an aperture within the main body of the sheet and a slot opening from a side of the device communication with the aperture in the sheet to allow the aperture to be accessible through the slot; and
      (iii) a detachable portion of the sheet extending over the dispensing portion said detachable portion being a perforated panel in the sheet defining a panel extending over the dispensing portion of the reservoir.

6. A device according to claim 5 wherein the panel completely covers the impermeable layer and the impermeable layer is provided with a tab by which it may be removed.

7. A device according to claim 1 wherein the sheet is provided with a slot for suspending the device on a sales display unit.

8. A device according to claim 1 wherein the suspending means is shaped so as to enable the device to be hung on a wardrobe rail.

9. A package comprising two of the devices of claim 1 placed side by side and detachably joined together at their contiguous sides by a detachable joint.

10. The package of claim 9 wherein the detachable joint is a pre-formed line of division.

11. The package of claim 9 wherein each of the detachably joined devices is a mirror image of the other.

12. A package for dispensing volatile material which comprises;
   (a) two devices for dispensing volatile material placed side by side and detachably joined together at their contiguous sides by a detachable point with each device being a mirror image of the other, each device comprising:
      (b) a reservoir containing volatile material, said reservoir having a dispensing portion from which vapor of the volatile material can diffuse into the surrounding atmosphere;
      (c) a removable impermeable layer for sealing said dispensing portion; and
      (d) a substantially flat and rigid sheet, said sheet having:
         (i) means for retaining the reservoir on the sheet when in use; and
         (ii) suspending means by which the device may be suspended in use, the suspending means including an aperture within the main body of the sheet and a slot opening from a side of the device communicating with the aperture in the sheet to allow the aperture to be accessible through the slot;
            wherein the slot of the suspending means of each detachably joined device opens toward the side of the device by which it is joined to the other of the detachably joined devices, whereupon the aperture within the main body of each device becomes accessible through its associated slot only when the devices have been detached from each other at the detachable joint.

13. A package for dispensing volatile material which comprises:
   (a) two devices for dispensing volatile material placed side by side and detachably joined together at their contiguous sides by a detachable joint with each device being a mirror image of the other, each device comprising:
      (b) a reservoir containing volatile material, said reservoir having a dispensing portion from which vapor of the volatile material can diffuse into the surrounding atmosphere;
      (c) a removable impermeable layer for sealing said dispensing portion; and
      a substantially flat and rigid sheet, said sheet having:
         means for retaining the reservoir on the sheet when in use; and
         (ii) suspending means by which the device may be suspended in use, the suspending means including an aperture within the main body of the sheet and a slot opening from a side of the device communicating with the aperture in the sheet to allow the aperture to be accessible through the slot;
            wherein the slot of the suspending means of each of the detachably joined devices opens toward the side of the device opposite to the side by which it is joined to the other of the detachably joined devices to make the aperture with the main body of either device accessible through its associated slot without first detaching the devices from each other.

* * * * *